(12) United States Patent
Scoseria et al.

(10) Patent No.: US 7,896,822 B2
(45) Date of Patent: Mar. 1, 2011

(54) MULTIPLE LITHOTRIPTER ELECTRODE

(76) Inventors: Jose P. Scoseria, Potomac, MD (US);
Anthony Lavigna, Beltsville, MD (US)

( * ) Notice: Subject to any disclaimer, the term of this patent is extended or adjusted under 35 U.S.C. 154(b) by 644 days.

(21) Appl. No.: 11/998,497

(22) Filed: Nov. 30, 2007

(65) Prior Publication Data
US 2008/0132810 A1  Jun. 5, 2008

Related U.S. Application Data

(60) Provisional application No. 60/861,757, filed on Nov. 30, 2006.

(51) Int. Cl.
*A61H 1/00*  (2006.01)
*H01T 13/14*  (2006.01)

(52) U.S. Cl. ............................................. 601/4; 313/125
(58) Field of Classification Search ........ 601/4; 29/854, 29/857; 313/125
See application file for complete search history.

(56) References Cited

U.S. PATENT DOCUMENTS

| | | | |
|---|---|---|---|
| 4,905,673 A | 3/1990 | Pimiskem | |
| 5,047,685 A | 9/1991 | Nowacki et al. | |
| 5,105,801 A | 4/1992 | Cathignol et al. | |
| 5,195,508 A | 3/1993 | Müller et al. | |
| 5,251,614 A | 10/1993 | Cathignol et al. | |
| 5,420,473 A | 5/1995 | Thomas | |
| 6,217,531 B1 | 4/2001 | Reitmajer | |
| 6,849,994 B1 | 2/2005 | White et al. | |

*Primary Examiner* — Long V Le
*Assistant Examiner* — Michael T Rozanski
(74) *Attorney, Agent, or Firm* — Ober, Kaler, Grimes & Shriver; Royal W. Craig

(57) ABSTRACT

A universal spark gap electrode with inner conductor formed as an elongate rod, an insulative sheath fit over the inner conductor, and an inner electrode tip soldered or brazed into the inner conductor. The inner conductor passes through an adapter and into an annular base with a spark gap cage and second electrode tip mounted thereon. The adapter is equipped with a molded annular jacket-type adapter mounted exteriorly thereon for engagement with the connecting receptacle of a lithotripsy machine. The annular base has a double-threaded collar that couples over the insulative sheath, and the adapter body screw-couples over the threaded collar of the annular base. This, the annular base, adapter body and insulative sheath are screw-coupled together in a coaxial configuration. Once the electrode is connected, the electrode tips generate a spark at the spark gap that vaporizes a small quantity of water, which creates an acoustic shock wave, which can be focused into the tissue of the patient and at a focal point corresponding to the position of a kidney stone or the like. A main advantage of the foregoing design is that the adapter can easily be substituted and replaced by an alternately-configured adapter to mate with other brands of lithotripters.

8 Claims, 4 Drawing Sheets

MULTIPLE LITHOTRIPTER ELECTRODE

CROSS-REFERENCE TO RELATED APPLICATION(S)

The present application derives priority from U.S. provisional application Ser. No. 60/861,757 filed 30 Nov. 2006.

BACKGROUND OF THE INVENTION

1. Field of the Invention

The present invention relates to lithotripsy equipment and, more particularly, to an improved electrode design that can be universally adapted for use with a range of lithotripters of various manufacturers.

2. Description of the Background

A lithotripter is a device that pulverizes kidney stones and gallstones by passing shock waves through a water-filled membrane that presses against the side of the patient. Extracorporeal shockwave lithotripters (ESWLs) in particular are used for treating kidney and biliary stones. The first ESWL lithotripter was developed in West Germany, and the US Food and Drug Administration (FDA) approved its use in the United States in Dec. 1984. Since then hundreds of thousands of patients have been treated. Lithotripters can use a number of methods of generating shock waves. Most typically, shock waves are generated by an electrode or "spark plug" placed at the focus of an ellipsoidal reflector. The spark from the plug vaporizes a small amount of water, creates a shock wave, and the ellipsoid reflector focuses each shock wave to a point about half a foot above it. A bombardment of successive shock waves has been found effective at disintegrating many stones including kidney stones.

The spark plug electrodes are usually constructed with an inner conductor which is surrounded by an insulating layer. The inner conductor extends beyond the insulation to an electrode tip. An opposing second electrode tip is spaced from the first electrode tip to provide a spark gap there between. A cage surrounds the electrodes and provides a conductor and necessary structure.

Examples of electrodes appear in several U.S. patents.

U.S. Pat. No. 5,105,801 to Cathignol et al. (Technomed) suggests that decreasing the resistance of the water decreases the latency time of the shockwave and actually increases the acoustic pressure.

U.S. Pat. No. 5,251,614 to Cathignol et al. discloses a lithotryptor electrode with closely-spaced discharge electrodes forming part of a discharge circuit having an inductance L and a capacitance C defining a critical resistance Rc equal to the square root of (L/C), U.S. Pat. No. 5,195,508 to Muller et al. (Dornier Medizintechnik) issued Mar. 23, 1993 shows a spark gap unit for lithotripsy with a pencil conductor with an inner electrode, and insulation that envelops the pencil conductor. An external cage conductor is formed with a bow and an outer electrode. The patent illustrates a hollow inner space inside the insulation of the pencil conductor, the space being open rearwardly for easy placement of a current-feeding plug (connected to the inner electrode).

U.S. Pat. No. 4,905,673 to Pimiskern issued Mar. 6, 1990 (Dornier System GmbH) shows a lithotripsy probe with an inner and an outer conductor with electrode tips. The two electrodes have tips of initially different diameter, the tips being flattened (truncated cones) and facing each other, the diameter of inner electrode being initially larger than the diameter of the tip of the outer electrode.

U.S. Pat. No. 6,217,531 to Reitmajer (ITS Medical Technologies & Services GmbH) issued Apr. 17, 2001 shows an adjustable electrode that self-measures the discharge voltage, compares it to a reference voltage, issues a correction signal, and operates an adjusting mechanism that repositions the electrodes, thus optimizing the spark gap.

U.S. Pat. No. 5,047,685 to Nowacki et al. issued Sep. 10, 1991 shows an electrode structure for lithotripters having inwardly turned tips with spaced confronting faces lying on opposite sides of the axis of the reflector.

Extracorporeal lithotripters are quite expensive, typically between $300,000 to $550,000, and their spark plug electrodes such as the foregoing are also expensive components. The rapid and frequent discharges of energy across the electrode tips has been found to erode and/or deteriorate the electrode tips, and replacement is often required.

U.S. Pat. No. 5,420,473 to Thomas issued May. 30, 1995 shows a partial solution in the form of a spark gap electrode assembly for lithotripters that allows easy replacement of both electrode tips without requiring manual adjustment of the spacing between the tips.

U.S. Pat. No. 6,849,994 to White et al. (Healthtronics) issued Feb. 1, 2005 is very similar to the above-noted '473 patent to Howard. Specifically, it shows an electrode assembly for lithotripters with a pencil conductor removably connected to an insulating layer. External threads on the pencil conductor cooperate with internal threads in a bore of the insulating layer to fixably secure the insulating layer in a desired position relative to the inner conductor and discharge electrode tip. FIG. 1 is an exploded view of the prior art '994 White et al. device. This spark plug-type electrode assembly 10 included an inner conductor 12 having an insulating layer 22 inserted thereon. A discharge tip 26 is inserted into the inner conductor 12 and extends from opening 30 at the distal end 32 of the insulating layer 22. A housing 34 has an internal bore 36 which allows the housing 34 to be disposed about the exterior surface 38 of the insulating layer 22. The housing is equipped with a plastic clip 40 that connects to an electrical power connection in the lithotripter. In this and other prior art electrodes the clip 40 is keyed to the lithotripter. The housing 34 is joined to a cage base 50 which serves as an outer conductor, conducting electricity through arms 52 to upper tip holder 54 which receives the second electrode tip 56. The cage base 50 surrounds bore 36 which extends over the insulating layer 22 as well as the upper housing 44, and its arms 52 are spaced apart providing access to a spark gap, which is the space directly between the electrode tips 26, 56. Accordingly, when a spark is generated, the acoustic shock waves may be transmitted from the spark gap through a reflector, and on through the tissue of a patient to break up the stones.

The '473 Thomas and White '994 patents suggests a partial solution to the problem in the form of a spark plug electrode having electrode tips that can be easily replaced. Nevertheless, with these and other known spark plug electrodes the electrode is keyed to the lithotripter and is available only as original equipment dedicated to a particular manufacturer's equipment. Spark plug electrodes from different manufacturers are not interchangeable. This effectively prevents replacement or substitution of the entire spark plug electrode assembly and compels purchase of an original equipment replacement Accordingly an improved electrode design is needed to allow adaptation to numerous lithotripters from various manufacturers.

SUMMARY OF THE INVENTION

It is therefore an object of the present invention to provide a spark gap electrode for lithotripsy machines with an interchangeable adapter that allows the same core electrode design to be interfitted to a variety of different machines from different manufacturers, most of which attempt to uniquely key their spark gap electrode to their particular machine by providing manufacturer-specific connecting receptacles.

It is another object to provide a spark gap electrode for lithotripsy machines as described above that employs a minimum of component parts.

It is still another object to provide a spark gap electrode as above that axially aligns and securely mounts the inner and outer electrode tips in an opposing relation within the spark gap.

In accordance with the foregoing object, the present invention is an improved universal spark gap electrode for use with a variety of lithotripsy machines having different connecting receptacles. The spark gap electrode generally comprises an inner conductor formed as an elongate rod and defined by a threaded receptacle at one end. An insulative sheath is press-fit over the inner conductor, the sheath being formed as a tubular covering for a major portion of the inner conductor. The insulative sheath has a screw threaded section and a pair of O-rings spaced along its length. An inner electrode tip is soldered or brazed into a distal receptacle of the inner conductor, protruding outward past the sheath, and the inner conductor/insulative sheath/electrode tip assembly is inserted through an adapter having a clip mounted exteriorly thereon for engagement with the connecting receptacle of a lithotripsy machine. The inner conductor within the insulative sheath passes through the housing, into an annular base, and into a spark gap cage on the base. The annular base has a double-threaded collar that screw-couples into the housing, and the insulative sheath likewise screw-couples into the threaded collar of the base. A second electrode tip is screw-inserted into the end of the spark gap cage of the base, and the two electrode tips remain opposed and coaxially spaced within the spark gap of the cage. Thus, once electrically connected, the electrode tips generates a spark at the spark gap that vaporizes a small quantity of water, which creates an acoustic shock wave, which can be focused into the tissue of the patient and at a focal point corresponding to the position of a kidney stone or the like. A main advantage of the foregoing design is that the adapter can easily be substituted and replaced by an alternately-configured adapter to mate with other brands of lithotripters.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DETAILED DESCRIPTION OF THE PREFERRED EMBODIMENTS

The present invention is an improved electrode design for lithotripsy that can be universally adapted for use with a range of lithotripters of various manufacturers.

Figure 1:
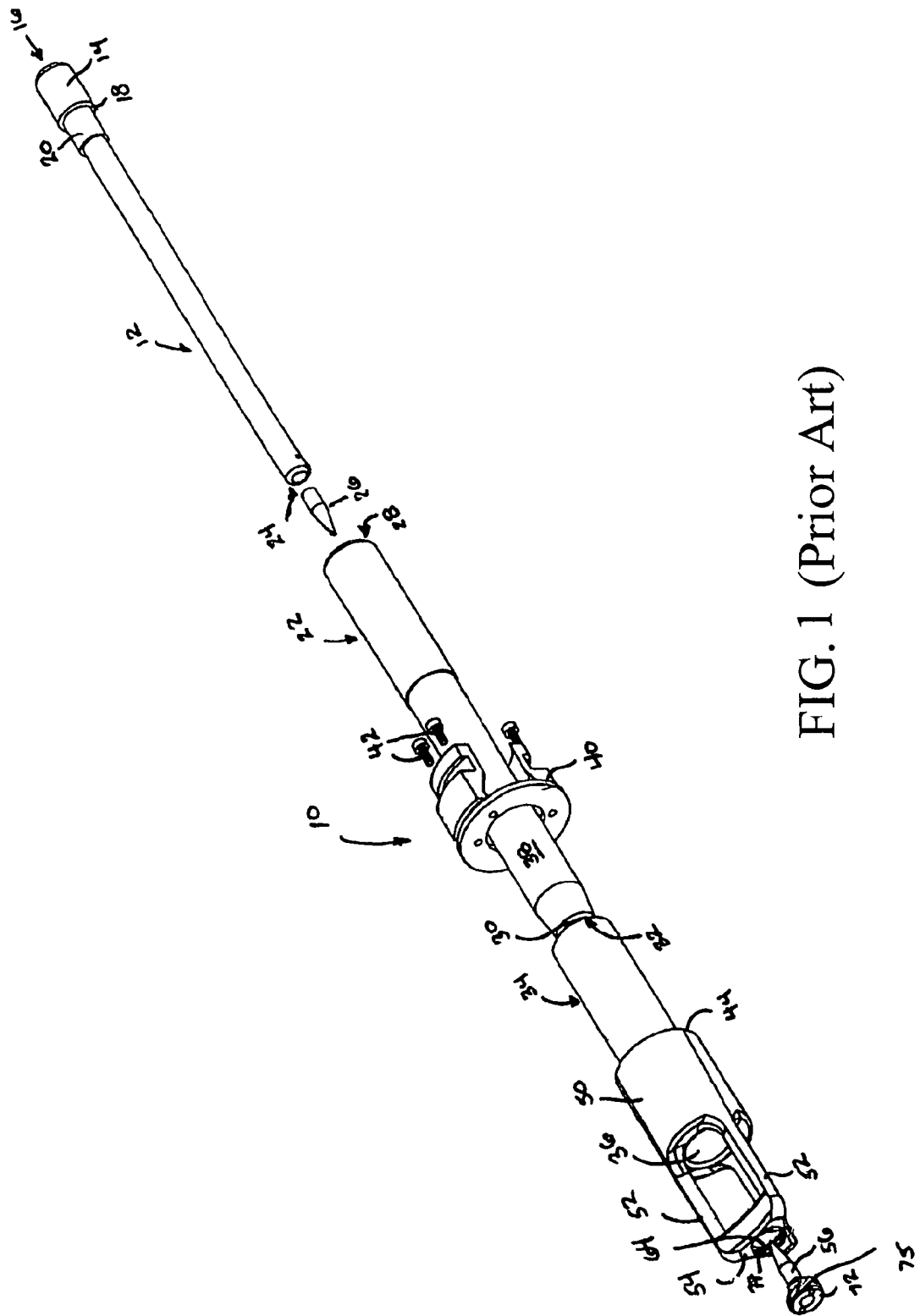
FIG. 1 shows an exploded view of a prior art spark plug-type electrode assembly 10 from U.S. Pat. No. 6,849,994 to White et al. issued Feb. 1, 2005.
Figure 2:
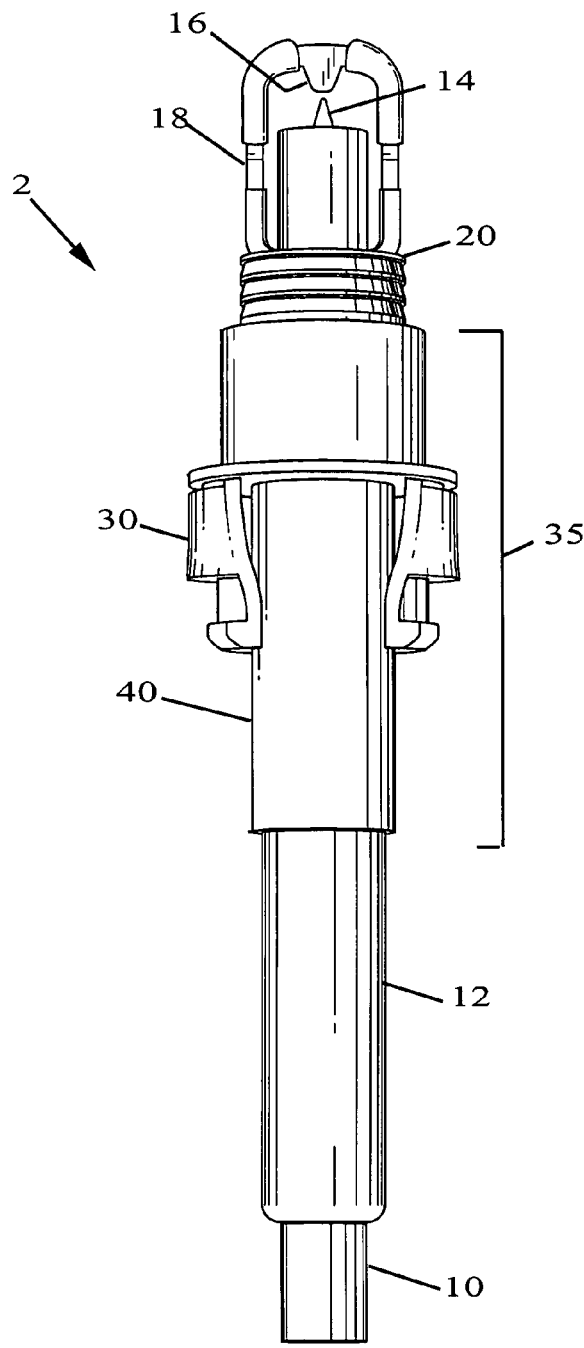
FIG. 2 is a front perspective view of the universal electrode 2 according to the present invention.

FIG. 2 is a front perspective view of the universal electrode 2 according to the present invention.

The universal electrode 2 generally comprises an inner conductor 10 that is ensheathed in an insulator 12, the insulator 12 being press-fit onto the inner conductor 10. The inner conductor 10 extends through the insulator 12 to an inner electrode tip 14 which protrudes nominally outward from the insulator 12. An opposing outer electrode tip 16 is coaxially spaced from the inner electrode tip 14 to provide a spark gap there between. A cage 18 surrounds the electrodes 14, 16 and provides a conductor and supporting structure therefore. The cage 18 is joined to a base 20, and the base 20 is attached to an adapter 35 that covers the exterior of the insulator 12. The adapter 35 includes a clip 30 that is fixedly attached about an adapter body 40, and the clip 30 defines a coupling that is keyed to a particular lithotripter. In accordance with the present invention, the adapter 35 (inclusive of clip 30) and adapter body 40 are interchangeable as a unit, easily disconnected (as will be described) from the remaining components. The clip 30 may be a molded plastic component attached to the adapter body 40. In the illustrated embodiment, the clip 30 is a molded plastic sleeve compression fit onto a brass adapter body 40, these two components comprising the adapter 35 that may be varied depending in the intended lithotripter for which it is intended. A variety of adapters 35 with different external configurations (including different clips 30) but common internal configurations (to all fit on a common adapter body 40) are made available, and the adapter 35 and adapter body 40 may be easily interchanged with an alternate clip 30/adapter body 40 to thereby accommodate numerous lithotripters from various manufacturers. This effectively allows replacement or substitution of the entire spark plug electrode assembly 2 using this standard configuration, with only the adapter 35 (inclusive of clip 30) changing from unit to unit.

Figure 3:
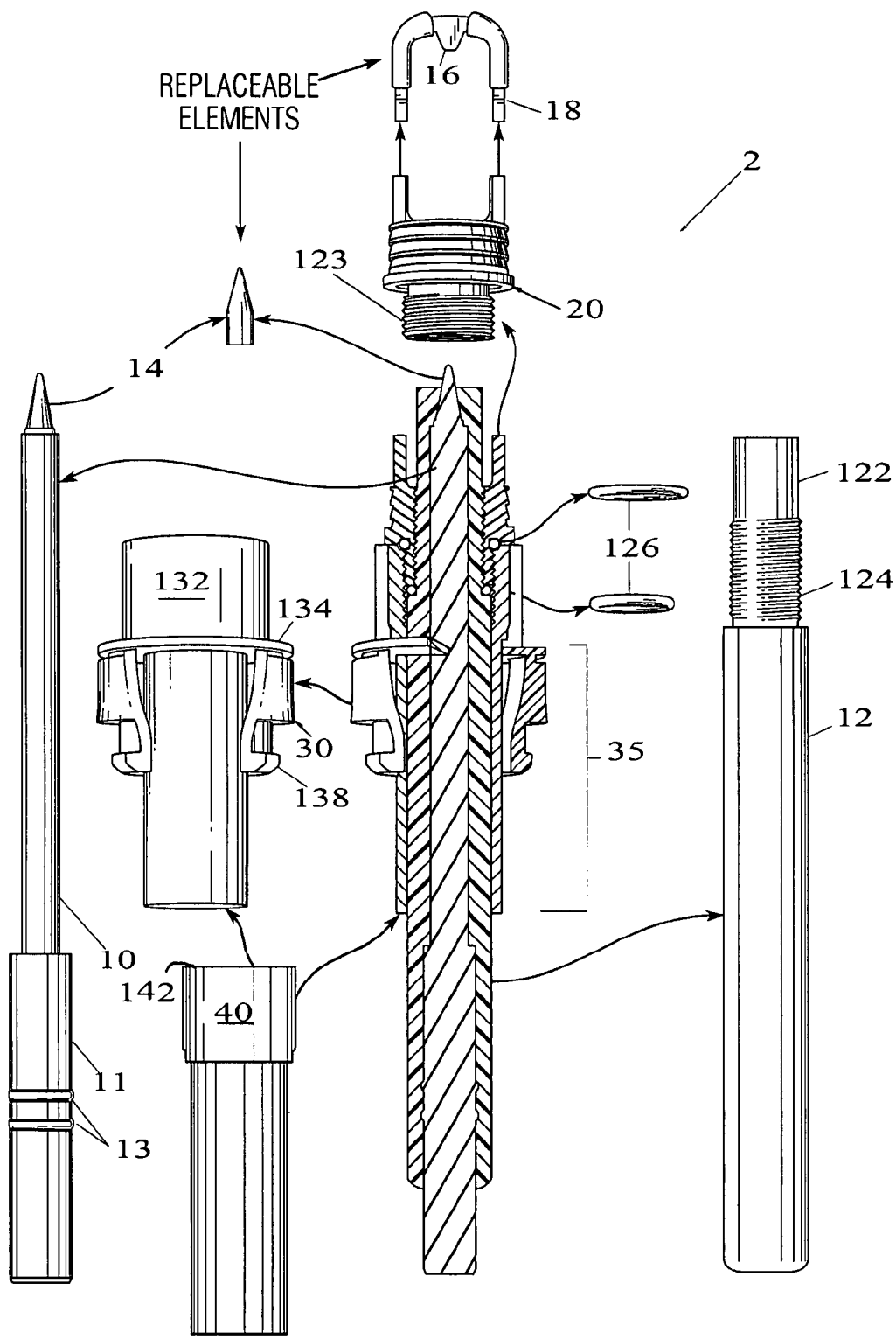
FIG. 3 shows an exploded perspective view of the universal electrode 2 of FIG. 2.

FIG. 3 shows an exploded perspective view of the universal electrode 2 of FIG. 2. The inner conductor 10 comprises a cylindrical brass rod that protrudes to a distal receptacle into which the inner electrode tip 14 is soldered or brazed. The insulator 12 comprises a cylindrical plastic (Delrin™ or the like) ferrule with internal through-bore. The inner conductor 10 is inserted lengthwise through the bore of the insulator 12 and is press-fit thereon such that the blunt end protrudes on one side and the inner electrode tip 14 protrudes on the other, the majority of the inner conductor 10 remaining ensheathed inside the insulator 12. The inner conductor 10 is preferably formed with a base section 11 of greater diameter that forms a shoulder which seats against a conforming shoulder within the through bore of the insulator 12. In addition, the base section 11 of inner conductor 10 is preferably formed with surface features to ensure a secure press-fit, and the two annular ribs 13 serve this purpose.

The exterior of the insulator 12 is defined by a cylindrical body with substantially uniform diameter along a majority of its length, and leading into a section of reduced diameter 122. The section of reduced diameter 122 at the junction is defined by a plurality of screw threads 124 for screw-coupling into the adapter body 40. The reduced diameter section 122 is dimensioned to fit snugly inside and through the adapter body 40. In addition, a pair of O-rings 126 encircle the cylindrical body of insulator 12 in advance of the screw-threads 124 to provide a fluid seal within the adapter body 40. O-rings 126 are preferably seated within annular notches defined in the body of insulator 12. Again, the inner electrode tip 14 protrudes slightly outward from insulator 12.

The adapter 35 comprises both the adapter body 40 and clip 30 which is mounted thereon, and while for purposes of illustration the clip 30 is formed as a discrete molded component attached to the adapter body 40, one skilled in the art should understand that the entire adapter 35 may be formed as one unitary component. The adapter body 40 comprises a hollow cylindrical length of brass tube with internal screw-threads at the end 132. The clip 30 is formed with a through-hole and is friction fit overtop adapter body 40. If desired, the clip 30 may additionally be bonded to adapter body 40.

The clip 30 is defined by three separate sections, including a cylindrical section 132 leading to a flange 134, and a detent clip 138 extending from the opposite side of the flange 134. The cylindrical section 132 fits over the internally-threaded end 142 of adapter body 40 as a collar, and abuts the base 20 when the base 20 is screw-inserted into the adapter body 40. The flange 134 limits insertion of the electrode 2 into the lithotripter. The collar 136 fits snugly into the lithotripter for stability, and locks the electrode therein. As shown, the illustrated detent clip 138 is a raised resilient annular member with an outwardly disposed lip for snap-fit insertion into one particular brand of lithotripter. Other lithotripter brands employ different locking mechanisms and the adapter 35 can easily be configured to mate with other brands of lithotripters.

When the base 20 is screw-inserted into the adapter body 40 the inner electrode tip 14 extends into the base 20 and out the other side, extending into the cage 18 opposite outer electrode tip 18. The cage 18 and outer electrode tip 16 are formed as an integral component attached, such as by welding, to the base 20 as shown in FIG. 3. This renders the cage 18 and outer electrode tip 16 replaceable as is the inner electrode tip 14. The insulator 12, adapter 35 (with exemplary clip 30 and adapter body 40), base 20 and cage 18, and outer electrode tip 16 form a precision-axially-aligned structure. The distal male screw-coupling 123 of base 20 threads into the threaded aperture 140 at one end of adapter body 40. Note that both inner and outer surfaces of the threaded aperture 140 are threaded. The insulator 12 with internally-fit conductor 10 is inserted through the adapter body 40 (protruding inner electrode tip 14 first), and the threads 124 of insulator 12 are screw-inserted axially into the distal male screw-coupling 123 of base 20. One O-ring 126 circles the threads 123 of the base 20 and the other circles the threads of the insulator 12 to prevents water from entering the adaptor 35. This configuration axially aligns and securely mounts adapter 35, base 20 and cage 18, and outer electrode tip 16 together such that the inner and outer electrode tips 14, 16 are held in an opposing relation centrally in the aperture of cage 18.

Figure 4:
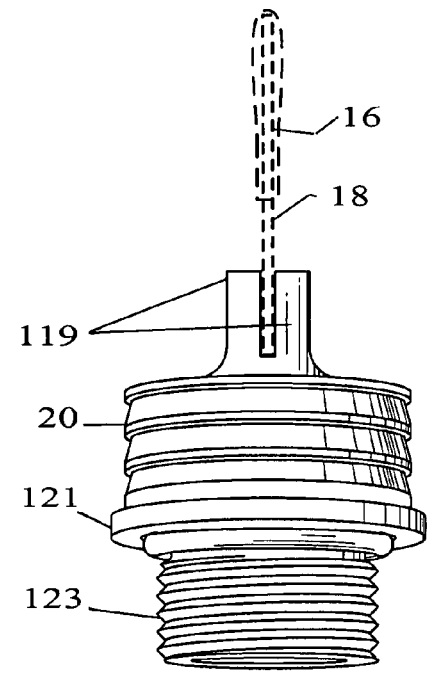
FIG. 4 is a side cross-section of the base 20 of FIG. 2.
Figure 5:
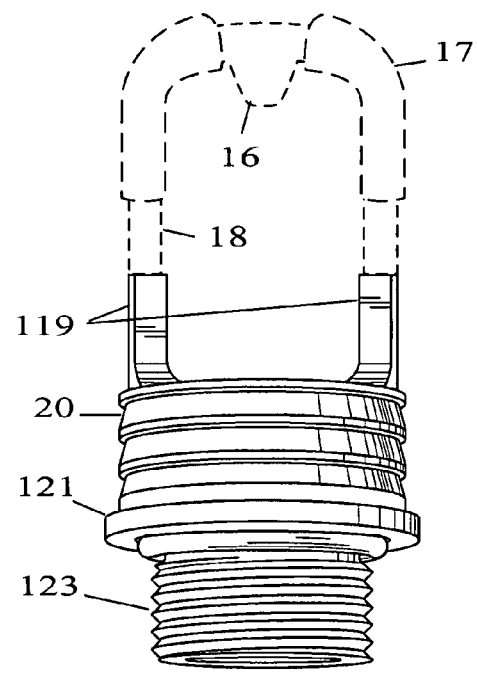
FIG. 5 is a side cross-section of base 20 of FIG. 4 rotated 90 degrees.

FIG. 4 is a side cross-section of the base 20, and FIG. 5 is a side cross-section of base 20 rotated 90 degrees. The base 20 is an annular brass member with a distal male screw-coupling 123 for insertion into the adapter body 40. The screw-coupling 123 leads to a flange that limits screw-insertion into the adapter body 40, and an annular notch is formed in advance of the flange to seat one of the O-rings 126. When assembled, the flange of base 20 is offset slightly from the shoulder defined by the base section 11 of the inner conductor 10. This shoulder limits screw-insertion of the base 20 as shown in FIG. 3 and a second O-ring 126 seals this intersection.

Referring back to FIGS. 4-5, the preferred embodiment of the base 20 includes a pair of opposing brackets 119 protruding up from the body of the base 20 to provide a mounting for the cage 18. Here the opposing brackets 119 are formed with a slots for receiving the ends of the prongs of cage 18, which are also welded therein. The cage 18 itself is a two-pronged support structure converging to a forward hub, the prongs of the cage being adapted to surround the opposed electrodes 14, 16 and yet provide open access to a partially-enclosed space therein. The cage 18 and base 20 also serve as a conductor to the outer electrode tip 16, which protrudes inward from the forward hub of cage 18, protruding into the partially-enclosed space in cage 18. Given this structure, the outer electrode tip 16 faces the inner electrode tip 14 within the confines of the partially-enclosed space in cage 18 to provide a spark gap there between. Accordingly, when a spark is generated, the acoustic shock waves may be transmitted from the spark gap through a reflector (not shown), and on through the tissue of a patient to break up stones.

Figure 6:
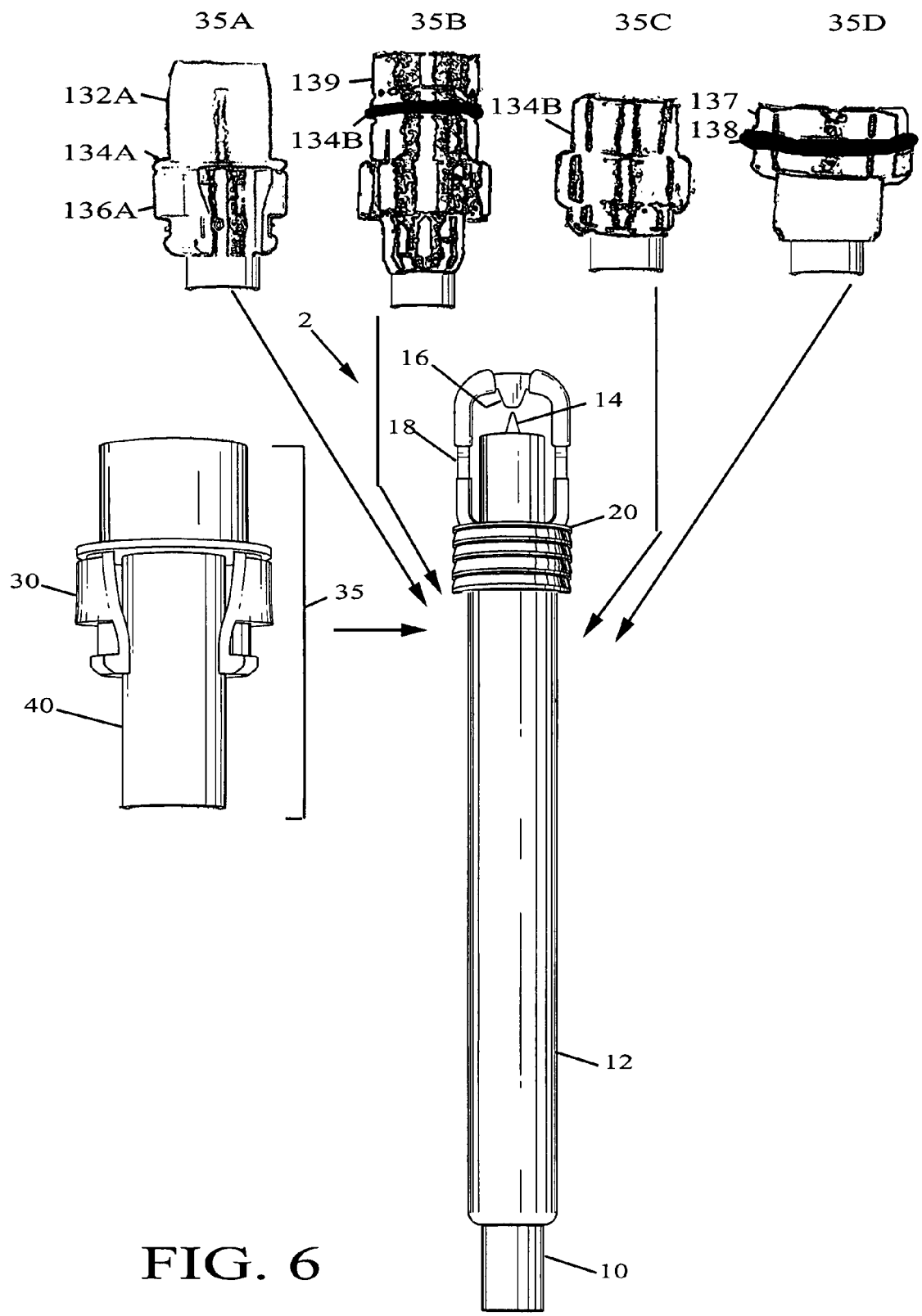
FIG. 6 illustrates a variety of other adapters 35A-35D designed for other brands of lithotripters.

FIG. 6 illustrates a variety of adapter assemblies 35, 35A, 35B, 35C and 35D each configured for a particular brand of lithotripters.

Adapter 35 (left) is as described above. However, the diameter and length of the inner conductor 10 and insulator 12 may vary with each lithotripter. The cage 18 surrounding the electrodes 14, 16 will remain substantially the same, except that its diameter may change. The adaptor 35 must be designed so that the electrode gap is precisely located at the focus of the partial elliptical bowl, e.g., the gap of the universal electrode 2 must be at the same place and of the same thickness (e.g., 0.5 mm) as the gap of the original equipment electrode supplied with the lithotripter.

Adapter 35A (top left) is similar but is formed with a prolonged and tapered cylindrical section 132A, and a longer raised collar 136A on the opposite side of the flange 134A.

Adapter 35B (top second from left) is formed as a unitary machined part with a pronounced flange 134B and seated O-ring 139 for sealed coupling to the lithotripter. Some lithotripters use a clip type adaptor as described previously while others use a metal ring-type adaptor. Adapter 35B is designed for the latter. In all such cases the universal electrode 2 is able to screw into a receiving hole in the appropriate lithotripter.

Adapter 35C (top second from right) is likewise formed as a unitary machined part similar to 35B but with a shorter flange 134B and no O-ring.

Adapter 35D (right) is likewise formed as a unitary machined part and includes as hort broad collar 137 and pronounced O-ring protruding sidewardly there from.

In all the foregoing examples all such adapters 35, 35A, 35B, 35C and 35D are uniform in certain respects including the same dimensioned through-hole, as illustrated in FIG. 3 to accommodate a uniform adapter base 40 (the latter likewise having internal threads to couple to base 20. Thus, the basic adapter 35 is the only component that must change for each brand of lithotripter (albeit it may be necessary to change the inner conductor 10 and insulator 12 slightly to accommodate other lithotripters since each lithotripter electrode may vary in overall length and diameter of the inner conductor 10), and it is easy to swap out various adapter assemblies (inclusive of adapter 35 and base 40).

In use, the proper adapter 35 is selected and installed as per the foregoing in accordance with the particular brand of lithotripter into which the electrode 2 will be installed. Once installed, the electrode 2 will generate a spark at the spark gap between electrode tips 14, 16 and inside cage 18. This spark vaporizes a small quantity of water, and the vaporization process emits an acoustic shock wave. The spark gap will be positioned at one focus of a partial elliptical reflector filled with a fluid, as known in the art. Thus, the acoustic shock wave is focused into the tissue of the patient and at a focal point corresponding to the position of a kidney stone or the like. A rapid succession of such shock waves is highly effective at disintegrating kidney stones.

Having now fully set forth the preferred embodiments and certain modifications of the concept underlying the present invention, various other embodiments as well as certain variations and modifications thereto may obviously occur to those skilled in the art upon becoming familiar with the underlying concept.

For example, it is possible to use one or two press fits instead of threads 123 for the coupling of the cage 18 to the adaptor 35 and/or for coupling of the insulator 12 to the cage 18. Also, the center conductor 10 might be formed with an integral inner electrode tip 14 rather than a receptacle with soldered or brazed tip 14. Finally, there are currently two categories of commercial lithotripters that require two different cage 18 diameters, and for manufacturing convenience it is presently envisioned that two different universal electrodes 2 will be offered with the two cage widths, one for the Lithotron™, HM3™, Medstone™ and Lithodiamond™ lithotripters, and one for the Medispec™ and Direx™ lithotripters. Therefore, in all such cases it is to be understood, that the invention may be practiced otherwise than as specifically set forth herein.

We claim:

1. A universal spark gap electrode for use with a variety of lithotripsy machines, said spark gap electrode comprising:
    an inner conductor formed as an elongate rod defined by a receptacle at one end;
    an insulative sheath formed as a tubular covering for said inner conductor, inserted lengthwise there over, and covering a major portion thereof to said receptacle, said insulative sheath having a length of uniformly-reduced diameter proximate said receptacle and external screw-threads around said reduced diameter length, and at least one O-ring encircling said reduced diameter length;
    a first electrode tip formed with a conical point at one end and a stem at another end, said stem being inserted into the receptacle of said inner conductor;
    an annular base having a removable spark gap cage protruding from one end thereof, said spark gap cage further comprising opposing prongs converging to support an inwardly-directed second electrode, said annular base also being formed with an internally and externally-threaded collar at another end thereof, the internal threads of said collar coupling onto the screw-threads of said insulative sheath;
    an annular adapter body having internal screw-threads coupled to the externally-threaded collar of said annular base; and
    a first adapter removably attached as a collar to said adapter body and further comprising an interlocking clip configured for releasably engaging a connecting receptacle of a first lithotripsy machine, said first adapter being removable and replaceable by a second adapter to mate with a second lithotripsy machine.

2. The universal spark gap electrode according to claim 1, wherein said inner conductor is formed with two sections of different diameter.

3. The universal spark gap electrode according to claim 1, wherein said inner conductor is formed with surface features for secure press-fit insertion into the insulative sheath.

4. The universal spark gap electrode according to claim 1, wherein said insulative sheath is formed with a distal socket.

5. The universal spark gap electrode according to claim 4, wherein said distal socket receives the first electrode tip.

6. The universal spark gap electrode according to claim 5, wherein said first electrode tip is threaded, and said distal socket is threaded to receive said threaded first electrode tip.

7. The universal spark gap electrode according to claim 1, wherein said interlocking clip further comprises opposing detent fingers.

8. The universal spark gap electrode according to claim 7, wherein said annular base comprises opposing mounting flanges at one end for supporting said removable spark gap cage and second electrode tip.

* * * * *